US009521955B2

(12) United States Patent
Ma et al.

(10) Patent No.: US 9,521,955 B2
(45) Date of Patent: Dec. 20, 2016

(54) SUBDURAL ELECTRO-OPTICAL SENSOR

(75) Inventors: Hongtao Ma, Bethesda, MD (US);
Theodore H. Schwartz, Scarsdale, NY (US); Jian-young Wu, Gaithersburg, MD (US)

(73) Assignees: CORNELL RESEARCH FOUNDTION, INC., Ithaca, NY (US); GEORGETOWN UNIVERSITY, Washington, DC (US)

(*) Notice: Subject to any disclaimer, the term of this patent is extended or adjusted under 35 U.S.C. 154(b) by 399 days.

(21) Appl. No.: 12/598,543

(22) PCT Filed: May 5, 2008

(86) PCT No.: PCT/US2008/062665
§ 371 (c)(1),
(2), (4) Date: Nov. 2, 2009

(87) PCT Pub. No.: WO2008/137851
PCT Pub. Date: Nov. 13, 2008

(65) Prior Publication Data
US 2011/0021885 A1    Jan. 27, 2011

Related U.S. Application Data

(60) Provisional application No. 60/915,864, filed on May 3, 2007.

(51) Int. Cl.
*A61B 5/00* (2006.01)
(52) U.S. Cl.
CPC .......... *A61B 5/0086* (2013.01); *A61B 5/0084* (2013.01); *A61B 5/4076* (2013.01); *A61B 2562/0233* (2013.01); *A61B 2562/046* (2013.01)

(58) Field of Classification Search
CPC ............ A61B 2562/046; A61B 5/0084; A61B 5/0086
USPC ....... 600/407, 476–477, 544, 545, 547, 300, 600/301; 607/57, 62
See application file for complete search history.

(56) References Cited

U.S. PATENT DOCUMENTS

| | | |
|---|---|---|
| 5,845,639 A | 12/1998 | Hochman et al. |
| 6,196,226 B1 | 3/2001 | Hochman et al. |
| 6,233,480 B1 | 5/2001 | Hochman et al. |
| 6,360,122 B1 | 3/2002 | Fischell et al. |
| 7,010,356 B2 * | 3/2006 | Jog et al. ...................... 607/116 |
| 7,089,059 B1 | 8/2006 | Pless |
| 7,151,961 B1 | 12/2006 | Whitehurst et al. |

(Continued)

FOREIGN PATENT DOCUMENTS

| | | |
|---|---|---|
| DE | 3812098 A1 | 11/1988 |
| JP | 7241284 A | 9/1995 |

(Continued)

OTHER PUBLICATIONS

International Search Report and Written Opinion for PCT/US2008/062665.
Ad-Tech, *Epilepsy & Neurosurgery Product Guide*, (2006), MKTG-3006-A4-Rev-J.
Blume, "Implanted EEG electrodes," (2005) http://professionals.epilepsy.com/page/surgery_electrodes.html.

(Continued)

*Primary Examiner* — Amanda Lauritzen Moher
(74) *Attorney, Agent, or Firm* — Scully, Scott, Murphy & Presser, P.C.

(57) ABSTRACT

A subdural electro-optical sensor system may include a substrate to which is attached an array of electrodes, light emitters, and light detectors. The sensor system may be sufficiently thin, flexible, sterile and biocompatible to be positioned subdurally.

19 Claims, 3 Drawing Sheets

(56) References Cited

U.S. PATENT DOCUMENTS

| | | | |
|---|---|---|---|
| 7,447,533 B1* | 11/2008 | Fang et al. | 600/310 |
| 7,747,318 B2* | 6/2010 | John | A61N 1/0529 607/2 |
| 7,805,174 B2* | 9/2010 | Carpenter et al. | 600/310 |
| 8,095,209 B2* | 1/2012 | Flaherty | 600/544 |
| 2003/0100845 A1 | 5/2003 | Eide | |
| 2004/0030258 A1 | 2/2004 | Williams et al. | |
| 2004/0039298 A1* | 2/2004 | Abreu | 600/558 |
| 2004/0082875 A1 | 4/2004 | Donoghue et al. | |
| 2004/0138536 A1 | 7/2004 | Frei et al. | |
| 2005/0203366 A1 | 9/2005 | Donoghue et al. | |
| 2006/0173259 A1 | 8/2006 | Flaherty et al. | |
| 2006/0224216 A1 | 10/2006 | Pless et al. | |
| 2007/0048731 A1* | 3/2007 | Colicos et al. | 435/4 |
| 2009/0054955 A1* | 2/2009 | Kopell et al. | 607/88 |
| 2009/0062685 A1* | 3/2009 | Bergethon et al. | 600/554 |
| 2012/0157804 A1* | 6/2012 | Rogers et al. | 600/345 |

FOREIGN PATENT DOCUMENTS

| | | |
|---|---|---|
| JP | 2006223503 A | 8/2006 |
| JP | 2006230955 A | 9/2006 |

OTHER PUBLICATIONS

Levi et al., "Integrated semiconductor optical sensors for cellular and neural imaging," *Applied Optics*, vol. 46, No. 10, Apr. 1, 2007, pp. 1881-1889.

Suh et al., "Blood volume and hemoglobin oxygenation response following electrical stimulation of human cortex," *NeuroImage*, vol. 31, (2006), pp. 66-75.

Zhao et al., "Focal Increases in Perfusion and Decreases in Hemoglobin Oxygenation Precede Seizure Onset in Spontaneous Human Epilepsy," *Epilepsia*, 48(11):2059-67, Nov. 2007, Epub Jul. 30, 2007.

\* cited by examiner

SUBDURAL ELECTRO-OPTICAL SENSOR

CROSS-REFERENCE TO RELATED APPLICATION

This is the national stage of International Application Ser. No. PCT/US2008/062665, filed May 5, 2008, which claims the benefit of U.S. Provisional Application No. 60/915,864, filed May 3, 2007, which is hereby incorporated herein by reference.

STATEMENT REGARDING FEDERALLY SPONSORED RESEARCH OR DEVELOPMENT

This invention was made with government support under 5R01NS049482-04 awarded by National Institute of Neurological Disorders and Stroke. The government has certain rights in the invention.

SUMMARY

Disclosed are systems and methods for monitoring brain activity, blood flow, and other processes in a patient using an intracranial sensor.

A sensor for intracranial monitoring may include a thin probe having multiple light sources, multiple light sensors, and multiple electrodes disposed therein or thereon. The probe may have a planar configuration. The probe may have an elongate configuration. The light sources may be infrared light sources. The light sensors may be sensitive to infrared light. The sensor may be implantable intracranially, superficial to the pia mater. The sensor may be implantable between the dura mater and the Arachnoid mater. The sensor may be positioned over a wide variety of brain regions.

DETAILED DESCRIPTION

1. Device Configuration

A. Pad Configuration

Figure 1:
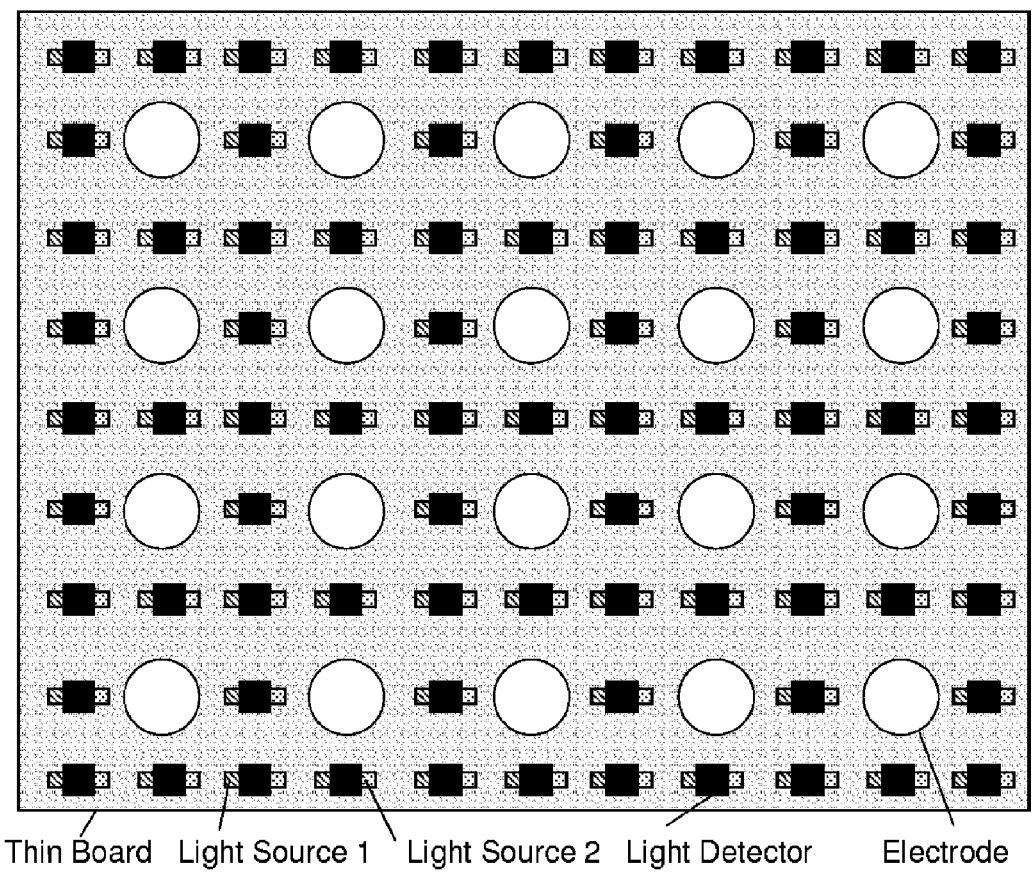
FIG. 1 schematically depicts an exemplary embodiment of a planar intracranial electro-optical sensor.

The electrodes and imaging components are arranged approximately in a plane (see FIG. 1 for a regular grid-like arrangement). The components may be embedded in a pad that is thin, flexible, sterile, and biocompatible to allow intracranial implantation, preferentially between the pia mater and the cranium. The pad can be of any shape, such as square, rectangular, circular, etc. The pad may have a thickness of about 300 micrometers or more; the electrical components attached to the pad may have a thick of about 500 micrometers or more; the total device thickness can be about 8000 micrometers or more, such as about 1000 micrometers. Pads such as those used in strip- and grid electrodes for long-term monitoring made by Ad-Tech Medical Instrument Corporation may be employed. Inter-electrode spacing may be in the range of 1 mm to 20 mm, or in the range of 5 mm to 15 mm, or in the range of 10 mm to 15 mm, or about 10 mm, or exactly 10 mm. Imaging components may be interspersed among the electrodes, as shown in FIG. 5.

Figure 3A:
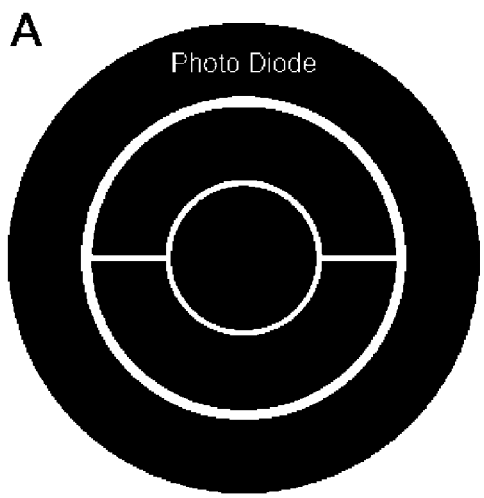
FIGS. 3A-3B schematically depict exemplary embodiments of integrated electro-optical sensors.
Figure 3B:
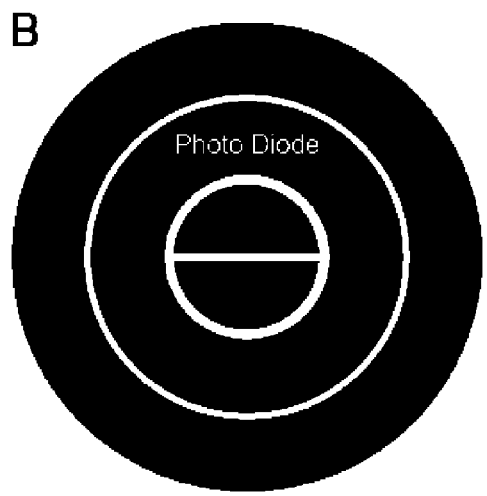
Figure 4:
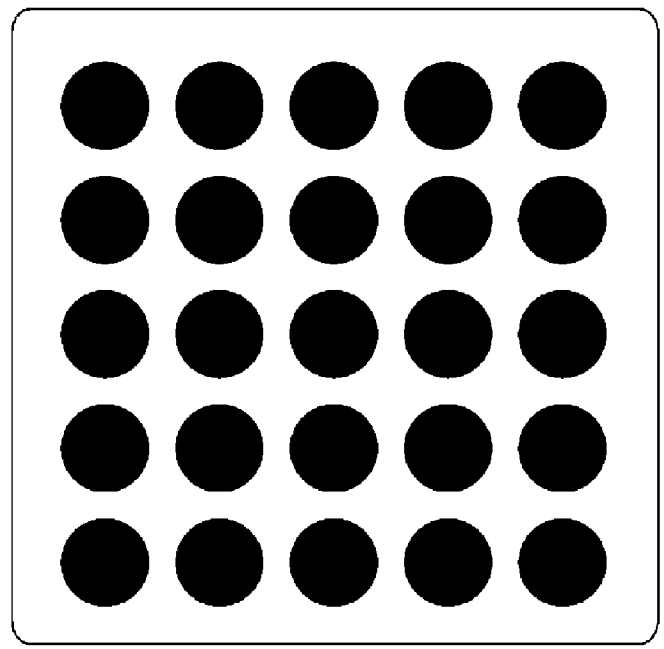
FIG. 4 schematically depicts an exemplary embodiment of a planar intracranial electro-optical sensor using integrated sensors of FIGS. 3A and/or 3B.

Alternatively, integrated electro-optical sensors may be employed. Examples are schematically shown in FIGS. 3A and 3B. Such integrated sensors may be arrayed on a pad, as shown in FIG. 4. Inter-sensor spacing may be as described above for inter-electrode spacing.

B. Probe Configuration

Figure 2:
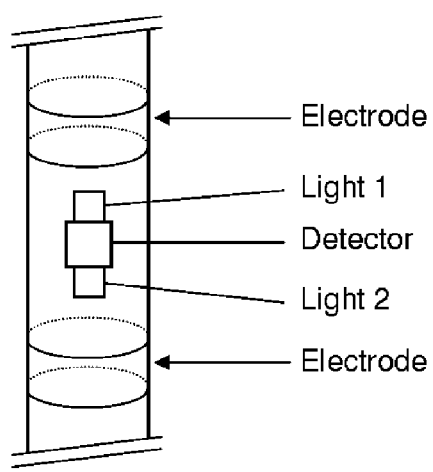
FIG. 2 schematically depicts an exemplary embodiment of an elongate intracranial electro-optical sensor.
Figure 5:
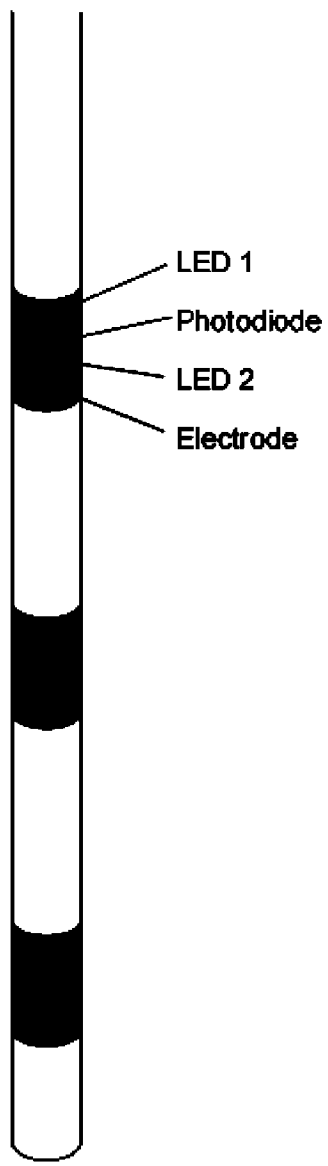
FIG. 5 schematically depicts another exemplary embodiment of an elongate intracranial electro-optical sensor.

The electrodes and imaging components are arranged along an elongate probe (exemplary embodiments schematically depicted in FIGS. 2 and 5). The probe is thin and sterile to allow minimally traumatic brain implantation, or may be a component of a deep brain stimulation unit. For example, the probe may have an outer diameter of up to 5 millimeters, up to 4 millimeters, up to 3 millimeters, up to 2 millimeters, and/or up to 1 millimeter, and/or in the range of about 1 millimeter and 2 millimeters; and a length suitable for reaching structures of interest within the brain. For example, the length may be in the range of about 5 centimeters to about 20 centimeters, about 5 centimeters to about 15 centimeters, about 10 centimeters to about 15 centimeters, and/or about 10 centimeters to about 13 centimeters. The electrodes may be provided as ring electrodes on the surface of the probe.

In some configurations, several small boards may be implanted at various locations. Each board may be delivered through a small craniotomy or another approach. Using several small boards instead of one larger board may eliminate the need for a large craniotomy to accommodate a larger board.

C. Localization of Implantation i. The pad conformation of the device is implanted between the pia mater and the cranium, preferentially between the dura and arachnoid layers. The device may be intracranially implanted superficial to the pia mater. The device may be intracranially implanted deep to the dura mater. The device bay be implanted in the subdural space. The device may be implanted in the subarachnoid space.

ii. A probe device could be implanted intracranially, in any area of interest.

For instance, a probe may be placed to monitor deep cerebral structures (i.e. amygdala, hippocampus and cingulum) which are characteristically involved in many medically refractory partial epilepsies.

Further, the probe could be implanted to measure brain activity in the substantia nigra to provide closed loop monitoring for deep brain stimulating device to treat a wide variety of disorders, such as Parkinson's, Tourette Syndrome, and/or other movement disorders. The probe could be implanted to monitor brain activity for detecting and/or treating epilepsy; obsessive-compulsive disorder, depression, and other psychiatric disorders; phantom limb pain, cluster headaches, and other pain disorders; traumatic brain injury; and stroke.

2. Components

A. Electrodes

The electrodes are designed for monitoring cortical electrical activity. The electrodes will be made from a substance that records electrical activity in the brain such as platinum, stainless steel or titanium, which is also suitable for implantation. For subdural implantation, thin disc-shaped electrodes will be used, with a diameter of 0.1-10 mm. For intracranial depth implantation, electrodes will be implanted along the length of a soft long, narrow tube, each electrode having a diameter of 0.1-10 mm.

B. EMR Sources

The electromagnetic radiation will be directly obtained from implantable LED and/or laser chips, or guided by optical fibers from external electromagnetic sources. For the pad configuration, the implantable EMR sources are thin (less than 0.5 mm) LED or laser chips, with an illumination range from 300-2000 nm. For a probe device, the EMR sources are either thin LED/laser chip or implantable optical fibers, which guide illumination from external illumination source.

C. Detectors

The optical signal will be recorded with photodiodes or CCD cameras. These devices convert optical signal into electrical signal, which can be simultaneously recorded with the neuronal activity. The thickness of the detectors is less than 0.5 mm and they are suitable for implantation in the subdural space.

When photodiodes are used, they may be coupled to an amplifier to generate signals indicative of detected light. An amplifier, such as used in WuTech Instruments' diode array systems may be used.

Light sources and detectors can be integrated into the light emitter/detectors. An integrated light emitter/detector may include one or more emitters and one or more detectors. For example, an integrated light emitter/detector may include one emitter and one detector, two emitters and one detector, one emitter and two detectors, two emitters and two detectors, etc. Integrated light emitter/detectors having at least two light emitters may be used to obtain spatially registered optical image maps using multiple wavelengths.

3. System

The cortex can be illuminated with different wavelengths sequentially, controlled by a computer. Alternatively, the illumination can be with white light and filters can be placed over the detectors to record at different wavelengths. The optical/electrical signal from each detector/electrode is amplified with its own parallel amplifier. The optical and electrical signals are simultaneously recorded with a computer for data analysis. The electrical activity maps and optical imaging maps will be generated by the software.

4. Optical Imaging Methods

The device could use at least two different types of Optical Imaging which would likely require different optical components:

A. ORIS (Optical Recording of Intrinsic Signal)

Optical signals detected at specific imaging wavelengths that map the brain according to perfusion-related and metabolic signals that reflect neuronal activity, including hemoglobin concentration and oxygenation changes, cytochrome oxidation changes, and light scattering caused by altered blood volume, blood flow, and cell swelling. For example, imaging at 610 nm emphasizes deoxyhemoglobin concentration changes, and imaging at 570 nm detects blood volume changes. ORIS have a tissue penetration of several hundreds of micrometers to a few millimeters. Components: LED, photodiodes. A light source ma "selectively" emit light of a wavelength, meaning that the source emits light of the identified wavelength, optionally light in a narrow hand (such as 1, 2, 5, or 10 nm in either direction) around the identified wavelength, and little or no light beyond the narrow hand.

B. DOT (Diffused Optical Tomography)

Recently developed technology which can perform continuous 3D imaging. This technique uses near-infrared (NIR) light, to detect not only absorption but also light scattering properties of biological tissues that correlate with neuronal activity. The tissue penetration of this imaging technology is up to 4 cm. Components: laserchips or fiber optics, photodiodes.

5. Methods

The device would be used for monitoring of brain function in patients prior to an invasive surgical treatment such as ablation of epileptic foci in drug refractory patients, or to monitor brain swelling in patients who have suffered a stroke or brain trauma, who may need a craniectomy to relieve pressure.

The device can be implanted in patients with epilepsy to help determine the location of the seizure onset and then to monitor brain functions such as motor, sensory, visual or language cortex. In addition, this device could be implanted in patients with head trauma to monitor blood flow and oxygenation. It could be implanted in patients with ischemia to monitor blood flow and oxygenation and neuronal activity.

The device could also serve as a sensing system as part of closed loop deep brain stimulation system in indications such as Parkinson's, Alzheimer's, or as stimulation to change a state of consciousness.

The device may be used to predict and/or detect onset of conditions that are preceded by optically-detectable changes. For example, hemodynamic changes that presage epileptic seizures may be detected prior to seizure onset (Zhao et al., "Focal increases in perfusion and decreases in hemoglobin oxygenation precede seizure onset in spontaneous human epilepsy." *Epilepsia* 48:2059-67 (Nov. 2007), hereby incorporated herein by reference). Such prediction/detection may be used, e.g., to warn the patient, warn a care provider, or administer a treatment. The device may include, or be functionally connected to, an electrical stimulator, such as a surface stimulator or deep brain stimulator, to administer electrical stimulation to the subject's brain to abate (i.e., stop or lessen) the seizure or other condition.

We claim:

1. A subdural electro-optical sensor system comprising: a subdural electro-optical sensor having a substrate to which is attached an array of electrodes and multiple integrated light emitter-detectors; wherein the subdural electro-optical sensor is sufficiently thin, flexible, sterile and biocompatible to be positioned subdurally, wherein the electrodes alternate with the multiple integrated light emitter-detectors in the array and wherein each integrated light emitter-detector comprises one light detector and two light emitters, each of the two light emitters are configured to emit light at different wavelengths.

2. The sensor system of claim 1, wherein the two light emitters are configured to selectively emit light at 570 nm and at 610 nm, respectively.

3. The sensor system of claim 1, wherein the one light detector in each of the integrated light emitter-detectors is a photodiode, and the system further comprises an amplifier coupled to the photodiode.

4. The sensor system of claim 1, wherein each wavelength is centered at a target wavelength and comprises a wavelength band having a bandwidth of less than 20 nm.

5. The sensor system of claim 1, wherein the electrodes are thin disc-shaped electrodes having a diameter of 0.1 mm to 10 mm.

6. The sensor system of claim 1, further comprising a processor connected to the electrodes and the integrated light emitter-detectors so as to receive signals from them indicative of light detected by the integrated light emitter-detectors and voltages measured by the electrodes.

7. The sensor system of claim 6, further comprising an electrical stimulator so coupled to the processor as to initiate electrical stimulation in response to the received signals.

8. The sensor system of claim 7, wherein the electrical stimulator is selected from a group comprising an electrical surface stimulator and an electrical deep brain stimulator.

9. The sensor system of claim 6, wherein the processor is further configured to control each of the two light emitters of the same integrated emitter-detector to sequentially emit the light.

10. The sensor system of claim 6, wherein the processor is further configured generate an alert based on the received signals.

11. The sensor system of claim 1, wherein a distance between two electrodes is in a range from 1 mm to 20 mm.

12. The sensor system of claim 11, wherein a distance between two electrodes is 10 mm.

13. The sensor system of claim 1, wherein the substrate has a thickness of about 300 microns.

14. The sensor system of claim 13, wherein the electrodes and the integrated light emitter-detectors have a thickness of 500 microns.

15. A method of monitoring a property of a subdural structure in a subject where a sensor system is subdurally and superficially implanted into the subject's pia mater, where the sensor system comprises a substrate to which is attached an array of electrodes and multiple integrated light emitter-detectors, wherein the sensor system is sufficiently thin, flexible, sterile and biocompatible to be positioned subdurally, wherein the electrodes alternate with the multiple integrated light emitter-detectors in the array and wherein each integrated light emitter-detector comprises one light detector and two light emitters, each of the two light emitters are configured to emit light at different wavelengths, the method comprising:
 emitting light from at least one of the light emitters of at least one of the multiple integrated light emitter-detectors upon the subdural structure;
 detecting light emitted from the subdural structure at the light detector in the same integrated light emitter-detectors which include the at least one light emitter that emitted light;
 measuring a voltage between an electrode and a reference potential or a second electrode; and
 generating one or more output signals indicative of the detected light and the measured voltage.

16. The method of claim 15, wherein at least one light emitter emits light selectively at 570 nm, at least one light emitter emits light selectively at 610 nm, and the method further comprises detecting a hemodynamic change from the detected emitted light.

17. The method of claim 15, wherein the sensor system further comprises an electrical stimulator, and the method comprises stimulating the subject's brain using the electrical stimulator if at least one of the detected light and the measured voltage indicate the need for brain stimulation.

18. The method of claim 15, wherein at least one light emitter continuously emits near-infrared light.

19. The method of claim 15, wherein each wavelength is centered at a target wavelength and comprises a wavelength band having a bandwidth of less than 20 nm.

* * * * *

UNITED STATES PATENT AND TRADEMARK OFFICE
CERTIFICATE OF CORRECTION

| | | |
|---|---|---|
| PATENT NO. | : 9,521,955 B2 | Page 1 of 1 |
| APPLICATION NO. | : 12/598543 | |
| DATED | : December 20, 2016 | |
| INVENTOR(S) | : Hongtao Ma et al. | |

It is certified that error appears in the above-identified patent and that said Letters Patent is hereby corrected as shown below:

On the Title Page

(73) Assignees Should Read: CORNELL RESEARCH FOUNDATION, INC., Ithaca, NY (US)
GEORGETOWN UNIVERSITY, Washington, DC (US)

In the Specification

Column 1, delete Lines 15-18 and insert:
--This invention was made with government support under Grant Number NS049482 awarded by the National Institutes of Health. The government has certain rights in the invention.--

Signed and Sealed this
Eleventh Day of April, 2017

Michelle K. Lee
*Director of the United States Patent and Trademark Office*